US011285269B2

(12) United States Patent
Boström

(10) Patent No.: US 11,285,269 B2
(45) Date of Patent: Mar. 29, 2022

(54) MEDICAMENT DELIVERY DEVICE ADAPTED FOR LONG TERM STORAGE

(71) Applicant: SHL MEDICAL AG, Zug (CH)

(72) Inventor: Anders Boström, Ingarö (SE)

(73) Assignee: SHL MEDICAL AG, Zug (CH)

( * ) Notice: Subject to any disclaimer, the term of this patent is extended or adjusted under 35 U.S.C. 154(b) by 203 days.

(21) Appl. No.: 16/348,847

(22) PCT Filed: Oct. 30, 2017

(86) PCT No.: PCT/EP2017/077744
§ 371 (c)(1),
(2) Date: May 9, 2019

(87) PCT Pub. No.: WO2018/091257
PCT Pub. Date: May 24, 2018

(65) Prior Publication Data
US 2020/0188605 A1    Jun. 18, 2020

(30) Foreign Application Priority Data

Nov. 18, 2016  (EP) .................................... 16199478

(51) Int. Cl.
*A61M 5/32*       (2006.01)
*A61M 5/20*       (2006.01)
(52) U.S. Cl.
CPC ........ *A61M 5/3202* (2013.01); *A61M 5/2033* (2013.01); *A61M 2005/2073* (2013.01)
(58) Field of Classification Search
CPC .............. A61M 5/3202; A61M 5/2033; A61M 2005/2073

(Continued)

(56) References Cited

U.S. PATENT DOCUMENTS

2003/0060776 A1   3/2003   Heiniger
2011/0034881 A1   2/2011   Bartha
(Continued)

FOREIGN PATENT DOCUMENTS

CN       1678362 A     10/2005
CN     103118723 A      5/2013
(Continued)

OTHER PUBLICATIONS

International Search Report and Written Opinion for Int. App. No. PCT/EP2017/077744, dated Jan. 26, 2018.
(Continued)

*Primary Examiner* — Brandy S Lee
*Assistant Examiner* — Nidah Hussain
(74) *Attorney, Agent, or Firm* — McDonnell Boehnen Hulbert & Berghoff LLP

(57) ABSTRACT

A medicament delivery device is presented having a housing, a medicament container holder arranged to accommodate a medicament container provided with a medicament delivery member, a power unit arranged to act on the medicament container for expelling a dose of medicament when activated, an activation mechanism operably connected to the power unit. The activation mechanism is capable of activating said power unit and includes a medicament delivery member guard movable in a longitudinal direction in relation to the housing. The activation mechanism also has a force element arranged to bias said medicament delivery member guard to a proximal extended position wherein said medicament delivery member is covered and has a locking mechanism operably arranged to lock the medicament delivery member guard in the extended position, where the locking mechanism has a number of locking elements connected to the medicament delivery member guard and flexible in a generally radial direction.

17 Claims, 16 Drawing Sheets

(58) Field of Classification Search
USPC .......................................................... 604/197
See application file for complete search history.

(56) References Cited

U.S. PATENT DOCUMENTS

2013/0317433 A1    11/2013  Fabien et al.
2018/0001025 A1*    1/2018  Sarkinen ............. A61M 5/2033

FOREIGN PATENT DOCUMENTS

| | | |
|---|---|---|
| CN | 105828851 A | 8/2016 |
| JP | 2012-500063 A | 1/2012 |
| JP | 2013-534164 A | 9/2013 |
| JP | 2015-517369 A | 6/2015 |
| KR | 2014-0050753 A | 4/2014 |
| KR | 2016-0042006 A | 4/2016 |
| TW | 201102057 A | 1/2011 |
| TW | 201127367 A | 8/2011 |
| TW | 201635999 A | 10/2016 |
| WO | 01/64270 A1 | 9/2001 |
| WO | 2012/022810 A2 | 2/2012 |
| WO | 2013/032389 A1 | 3/2013 |
| WO | 2015/047114 A1 | 4/2015 |

OTHER PUBLICATIONS

European Search Report for EP Application No. 16199478.5, dated Apr. 26, 2017.

* cited by examiner

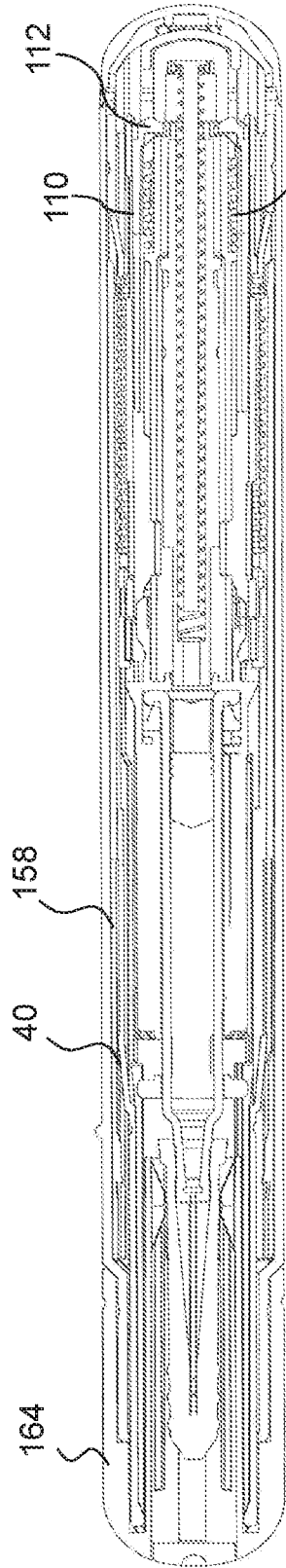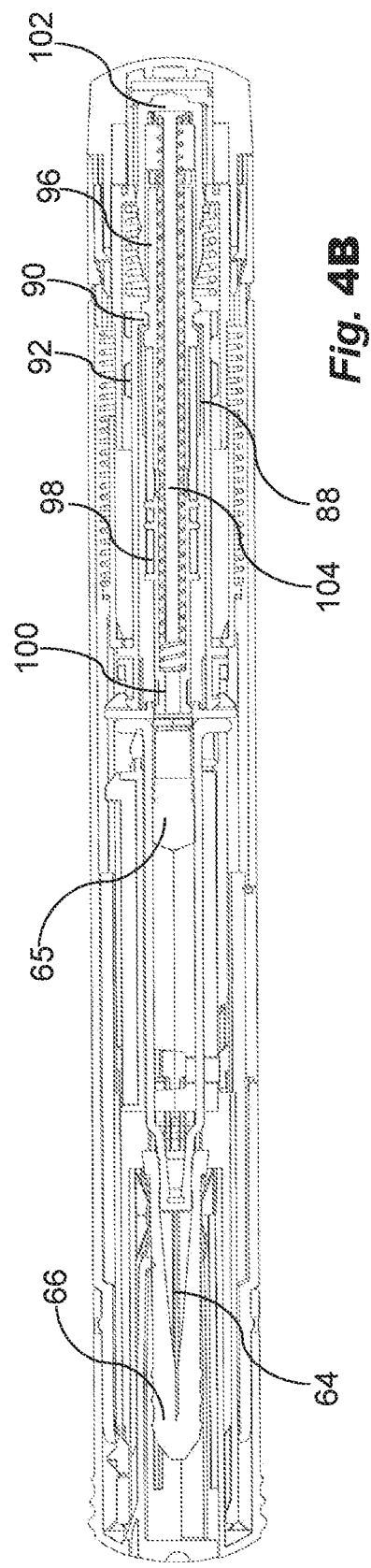
Fig. 4A
Fig. 4B

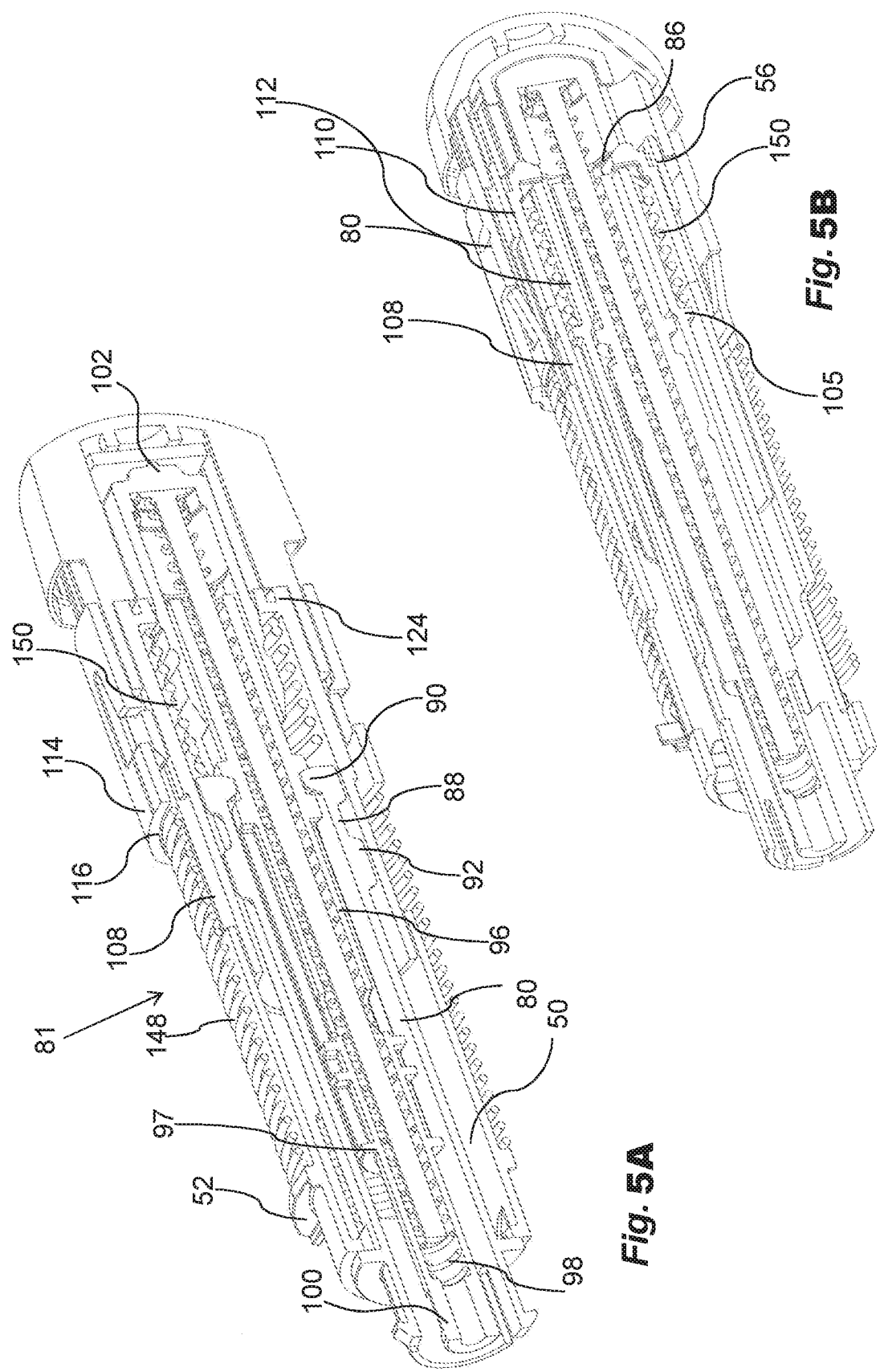

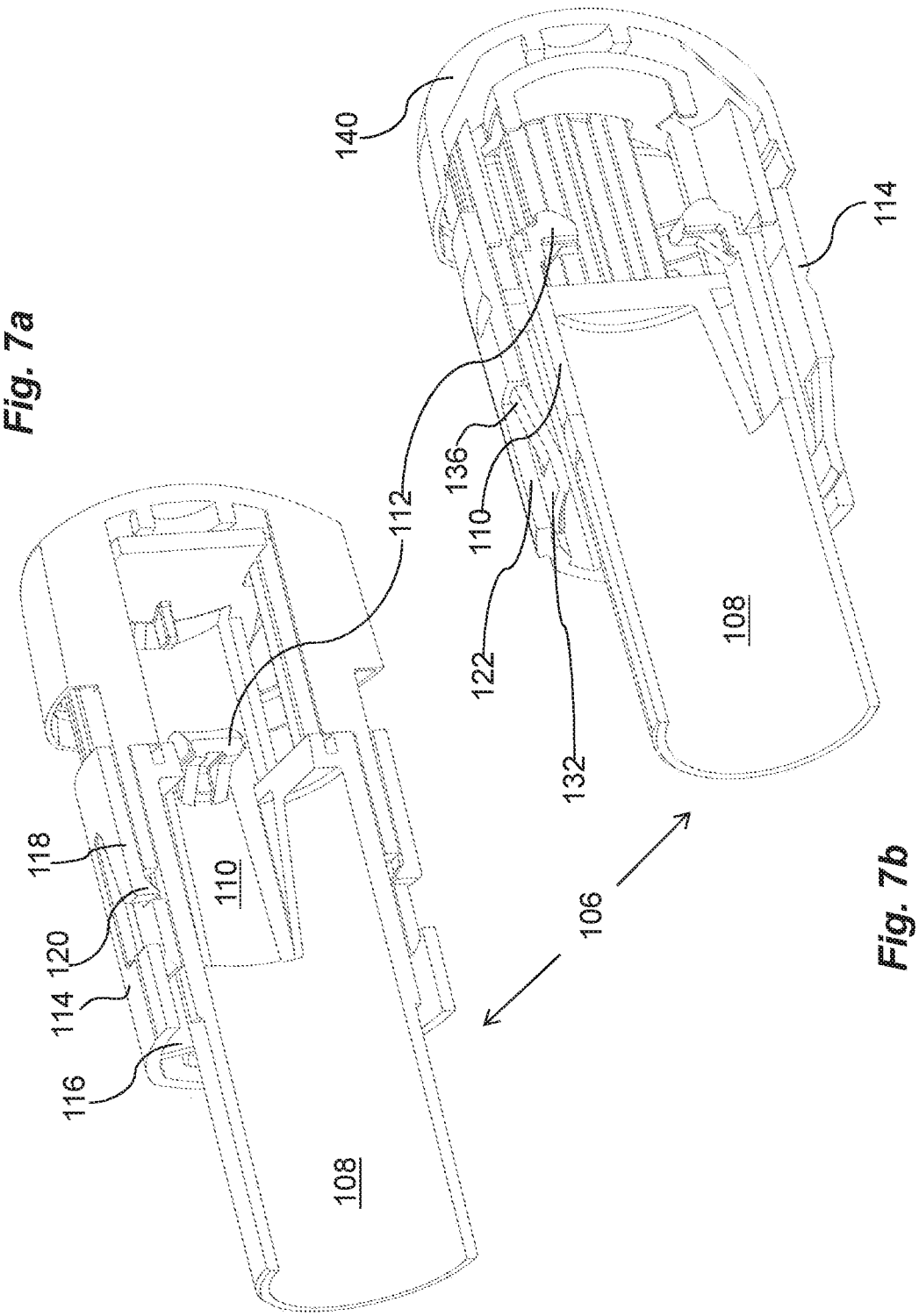

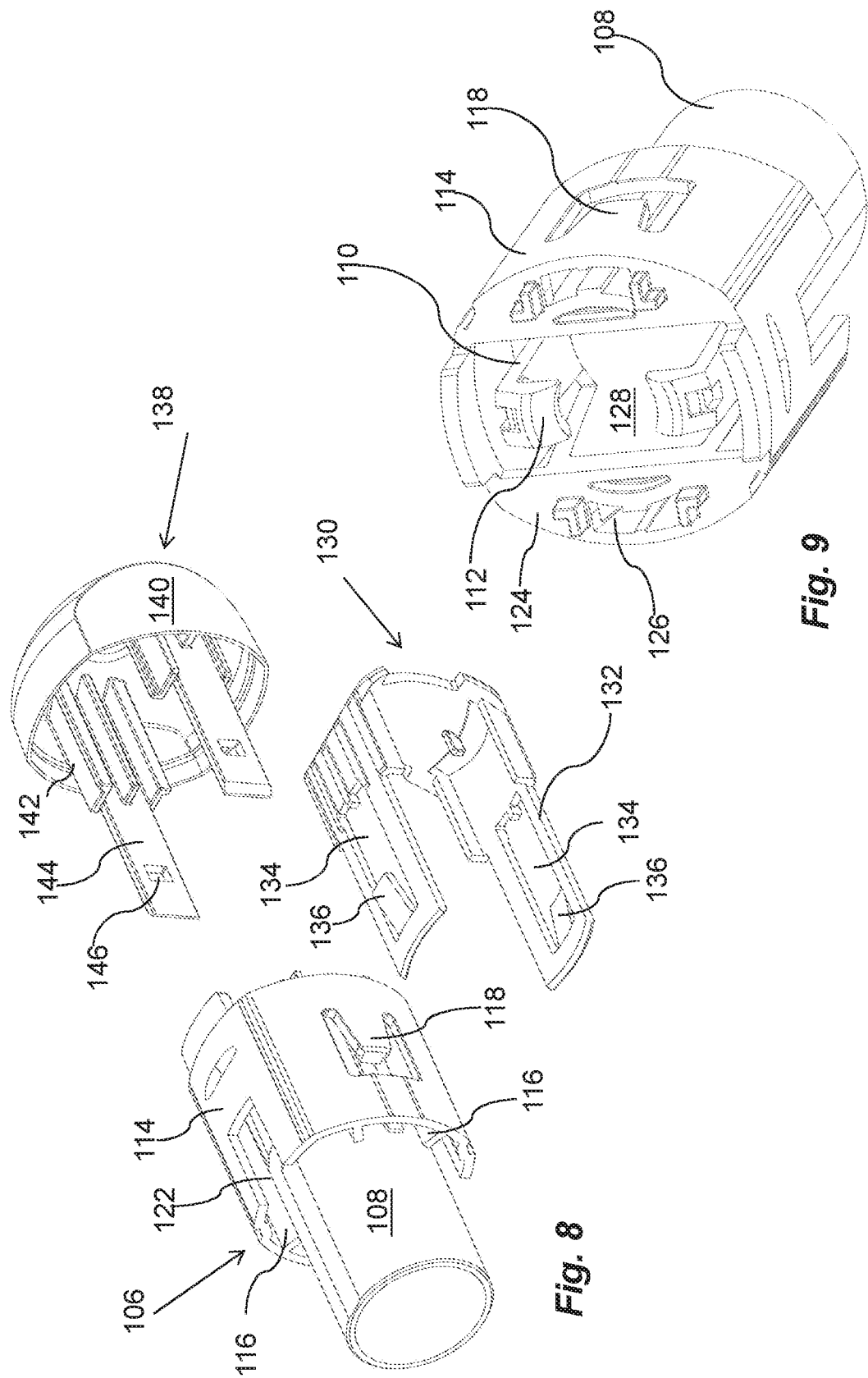

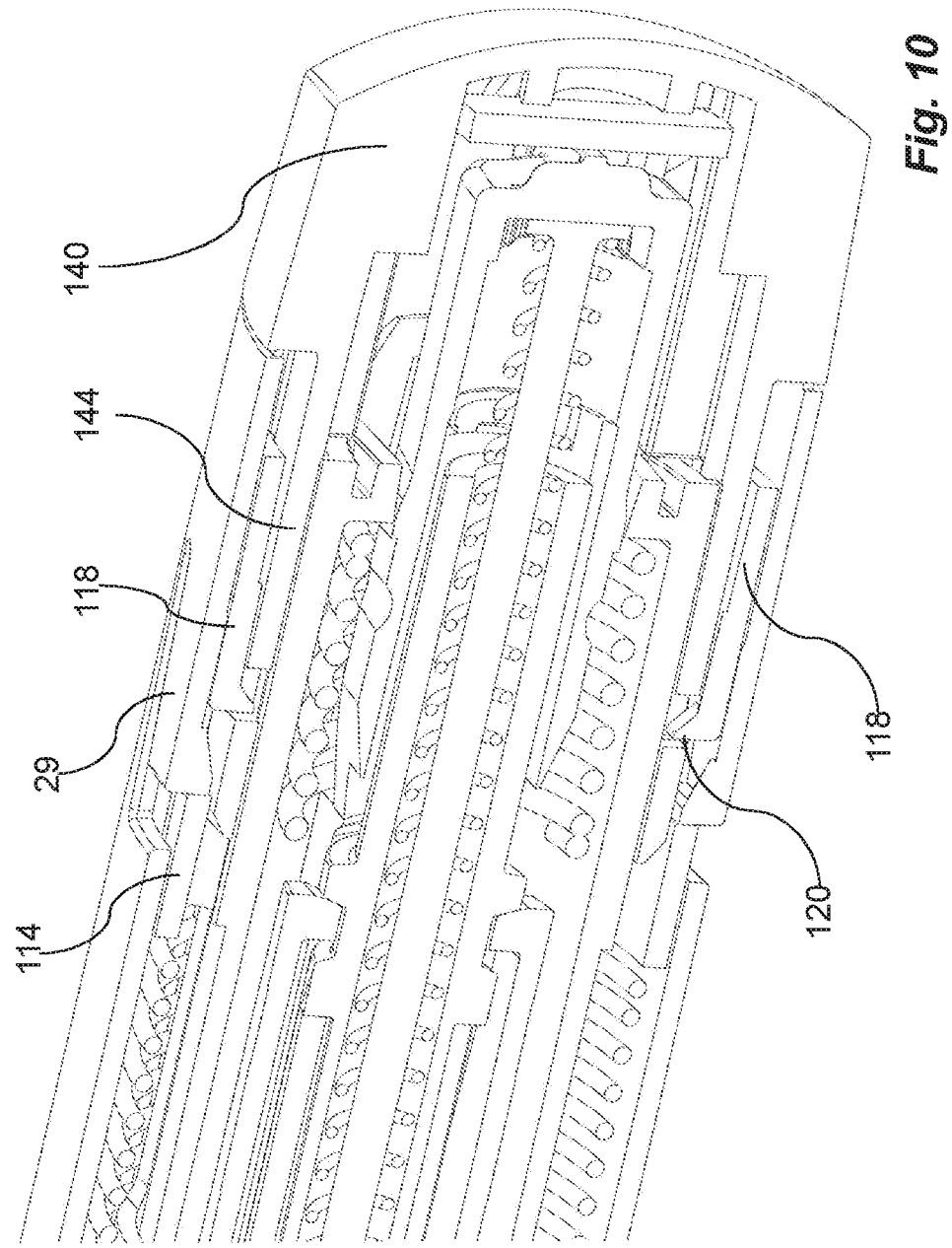

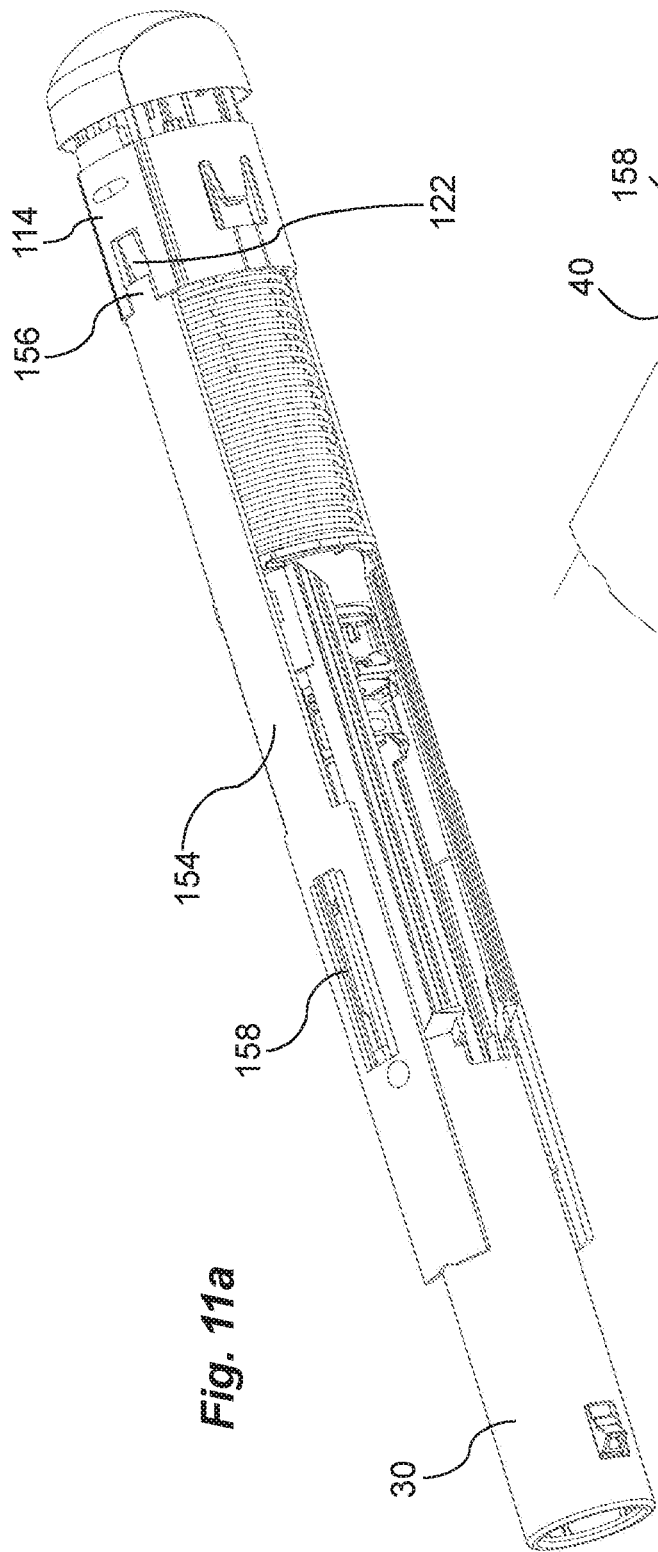
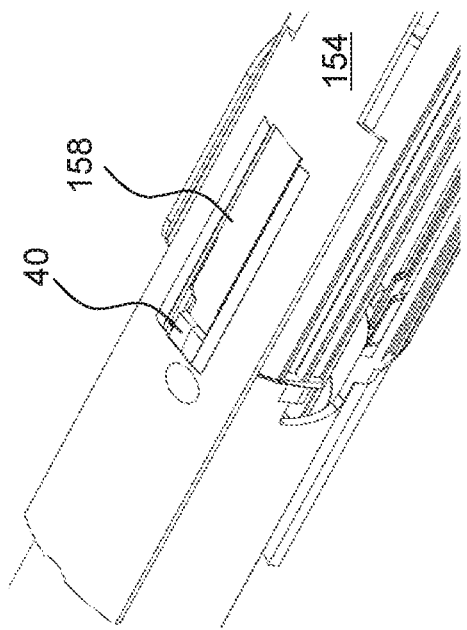
Fig. 11a
Fig. 11b

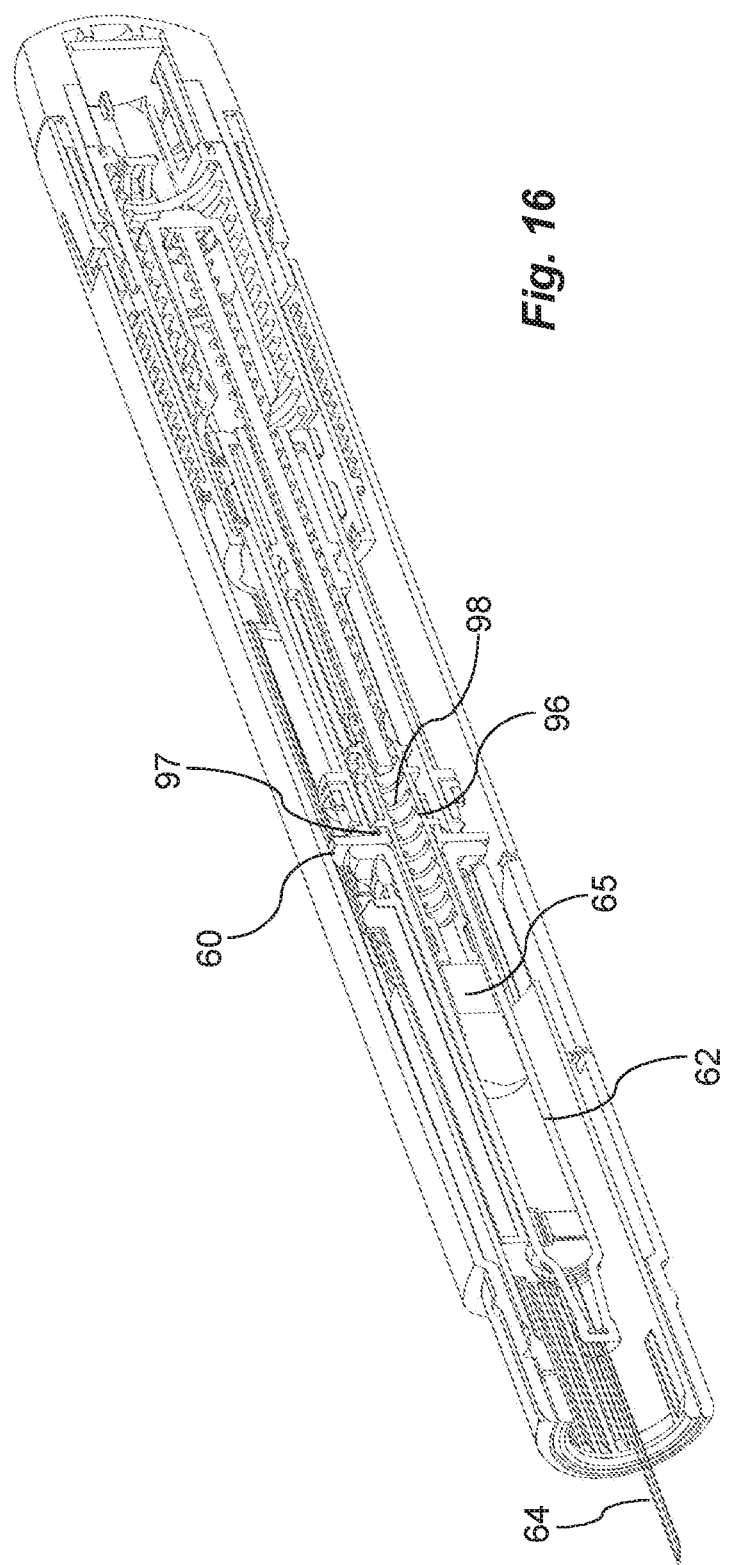

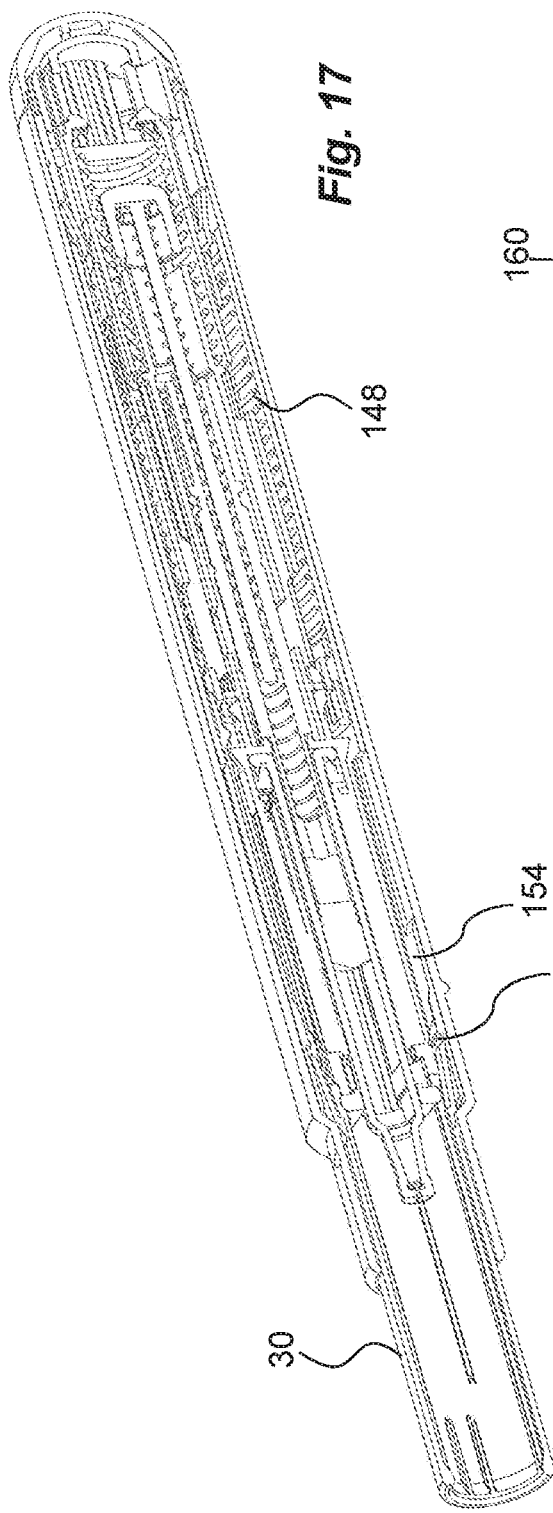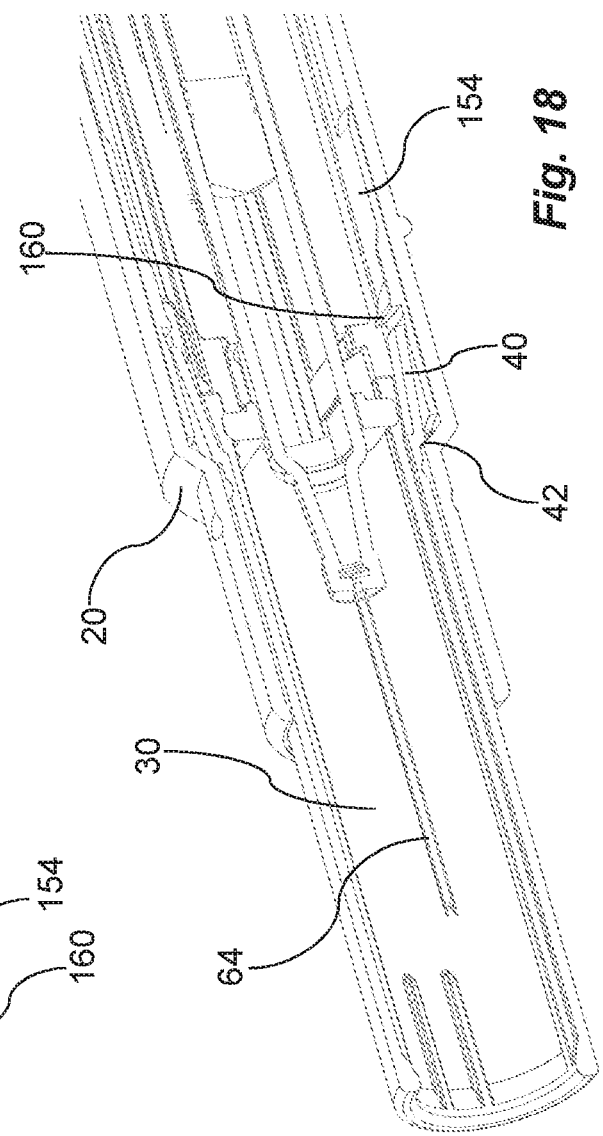

MEDICAMENT DELIVERY DEVICE ADAPTED FOR LONG TERM STORAGE

CROSS REFERENCE TO RELATED APPLICATIONS

The present application is a U.S. National Phase Application pursuant to 35 U.S.C. § 371 of International Application No. PCT/EP2017/077744 filed Oct. 30, 2017, which claims priority to European Patent Application No. 16199478.5 filed Nov. 18, 2016. The entire disclosure contents of these applications are herewith incorporated by reference into the present application.

TECHNICAL AREA

The present disclosure relates to a medicament delivery device comprising a large number of automatic features.

BACKGROUND

Medicament delivery devices with a number of features, in particular automated features, such as e.g. penetration, injection, withdrawal and covering of medicament delivery members have gained increasing popularity during the last 10-15 years.

Many of these highly automated medicament delivery devices, so called auto-injectors, are used for medicament that is to be taken during emergency situations and then often by unexperienced users. One very common medicament that is used in connection with auto-injectors is adrenalin that is administered for emergency treatment of anaphylaxis.

There are large numbers of these types of adrenaline medicament delivery devices placed in the society such as schools, museums, shopping malls etc. as emergency devices should a person suffer from an anaphylactic shock. Helping personnel such as teachers, guards, salespersons, etc. could then use an auto-injector with adrenaline to treat the person in chock.

These and many other medicament delivery devices with different types of drugs are often stored for long periods before being used. The majority of this type of medicament delivery device is made of components and elements of plastic material that may change properties when aging. Further, many functions of these devices comprise tongues, fingers, arms, levers and other elements that are arranged to flex in different directions for releasing or locking functional components.

For example the medicament delivery device disclosed in document WO 2013/032389 comprises a number of levers flexible in generally radial directions for holding and releasing a medicament container holder for performing a penetration, holding and releasing a plunger rod for performing an injection and for blocking the movement of a medicament delivery member guard after removal of the medicament delivery device from the medicament delivery site. Many of these levers, and in particular the levers that block the medicament delivery member guard are in a flexed, tensioned condition in their initial state and flex to a non-tensioned blocking condition when the medicament delivery member guard is to be blocked.

However, due to the effects of aging of plastic material and the tensioned condition, the levers may lose their flexing properties to a large extent, which may jeopardize the blocking capabilities of the levers, and thus may risk injuries if it is possible to move the medicament delivery member guard so that the medicament delivery member is exposed.

SUMMARY

The aim of the disclosure is to remedy the drawbacks of the state of the art medicament delivery devices and to provide a solution that will ensure full functionality even after longer storage periods.

The aim of the present disclosure is solved by a medicament delivery device comprising the features of the independent patent claims. Preferable embodiments of the disclosure form the subject of the dependent patent claims.

According to a main aspect of the disclosure, it comprises a medicament delivery device that may comprise a housing and a medicament container holder arranged to accommodate a medicament container. Further the medicament delivery device may comprise a power unit arranged to act on said medicament container for expelling a dose of medicament when activated as well as an activation mechanism operably connected to the power unit, capable of activating the power unit.

Preferably the activation unit comprises a medicament delivery member guard movable in a longitudinal direction in relation to said housing such that when a proximal end of the medicament delivery device is pressed against a dose delivery site, wherein the activation unit may comprise a force element arranged to bias the medicament delivery member guard to a proximal extended position wherein the medicament delivery member is covered.

The medicament delivery device may further comprise a locking mechanism operably arranged to lock the medicament delivery member guard in the extended position, wherein the locking mechanism may comprise a number of locking elements flexible in a generally radial direction. The locking mechanism may further comprise ledge surfaces to which the locking elements abut when the medicament delivery member guard is in the extended position, preventing any further movement of the medicament delivery member guard in the distal direction. This will effectively prevent any accidents of exposed medicament delivery members that otherwise may cause injuries like needle sticks.

According to a favourable solution, the medicament delivery device may be arranged with spaces connected to the housing in which the locking elements are positioned in a non-tensioned state in a delivery mode of the medicament delivery device. With this solution, the locking elements will not be in a tensioned state for longer periods of time when delivered and stored for future use. The material of the locking elements will thus not be affected and altered due to tensions in the material, thus ensuring proper functioning and flexing action of the locking elements when the medicament delivery device is used, even after longer times of storage.

The spaces may be recesses or cut-outs on the inner surface of the housing or on adjacent parts. According to one aspect of the disclosure, the spaces may be arranged on at least one separate component attached inside the housing of the medicament delivery device. With this solution it is easier to create the spaces or recesses than in the housing itself, because the latter is difficult from a manufacturing perspective. The separate component may be permanently or releasably attached to the housing.

Further, the separate component may comprise an elongated plate-shaped member, and the housing may be arranged with support elements preventing movement of the component when assembled. In that regard, the support elements may comprise a transversal stop element arranged to abut a proximal end of the at least one component. The transversal stop element may be comprised in the housing. This solution enables the plate-shaped member to be pushed or slid into the housing from a distal direction via the support elements until it is positioned by the abutment to the transversal stop element. Preferably the support elements may comprise longitudinally extending ledges arranged to support the at least one component in all transversal directions.

In order to fixate the plate-shaped member, the support elements may comprise a transversal stop element arranged to abut a distal end of the at least one component and according to one aspect, the support element may be comprised in a component attachable to the housing, such as an end cap that is attached to the distal end of the housing.

Further, the at least one element may also comprise the ledge surfaces of the locking mechanism. This has the advantage that the manufacturing is facilitated in that the manufacturing and the molds of the housing are less complex.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 4A is a cross-sectional view of the medicament delivery device of FIG. 1, FIG. 4B is a cross-sectional views of the medicament delivery device of FIG. 1, FIG. 5A is a cross-sectional view of a power unit comprised in the medicament delivery device of FIG. 1, FIG. 5B is a cross-sectional views of a power unit comprised in the medicament delivery device of FIG. 1, FIG. 7 is a detailed view of components comprised in the medicament delivery device of FIG. 1, FIG. 8 is a detailed view of components comprised in the medicament delivery device of FIG. 1, FIG. 9 is a detailed view of components comprised in the medicament delivery device of FIG. 1, FIG. 10 is a detailed view of components comprised in the medicament delivery device of FIG. 1, FIG. 11 is a detailed view of components comprised in the medicament delivery device of FIG. 1.

FIG. 16 is a view of a different functional stage of the medicament delivery device of FIG. 1

FIG. 17 is a view of a different functional stage of the medicament delivery device of FIG. 1, and FIG. 18 is a view of a different functional stage of the medicament delivery device of FIG. 1.

DETAILED DESCRIPTION

Figure 1:
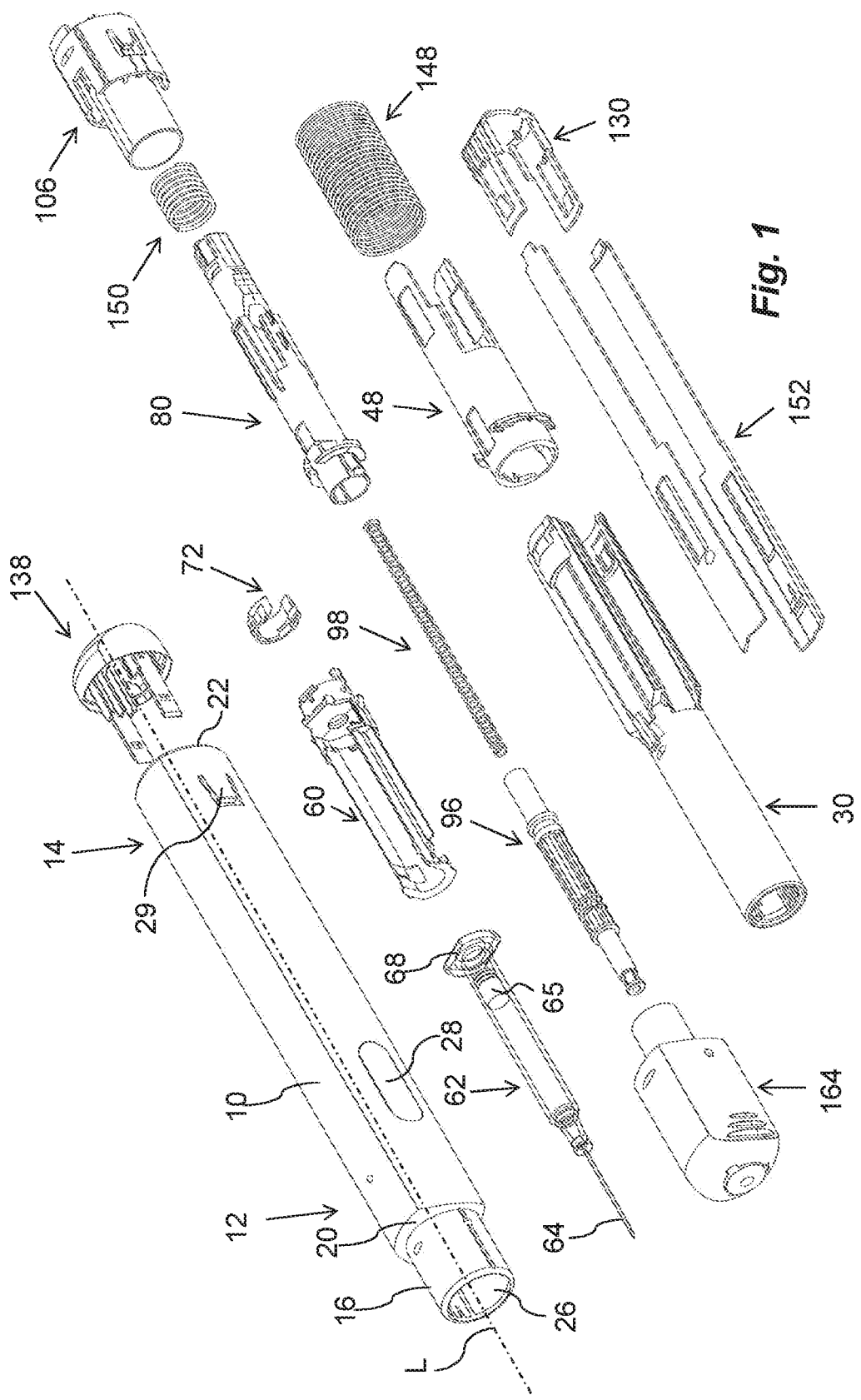
FIG. 1 is an exploded view of one embodiment of a medicament delivery device comprising the present disclosure.

The present disclosure relates to a medicament delivery device provided with an elongated housing 10 extending along a longitudinal axis L and having a proximal end 12 and distal end 14. The proximal end of the housing 10 is arranged with a tubular section 16, onto which a protective cap 164 is arranged to be releasably attached. A transversal transitional wall 20 is arranged between the tubular section 16 and the rest of the housing 10. The distal end 14 of the housing is arranged with a central opening 22, to which an end cap 138 may be attached. The distal area of the housing is arranged with arms 29 that are flexible in a generally radial direction, which arms are arranged with inwardly directed ledges for attaching the end cap 138 as will be described below. Further the proximal end 12 of the housing 10 is arranged with an opening 26. Moreover, an opening or window 28 is arranged on the side of the housing.

Figure 2:
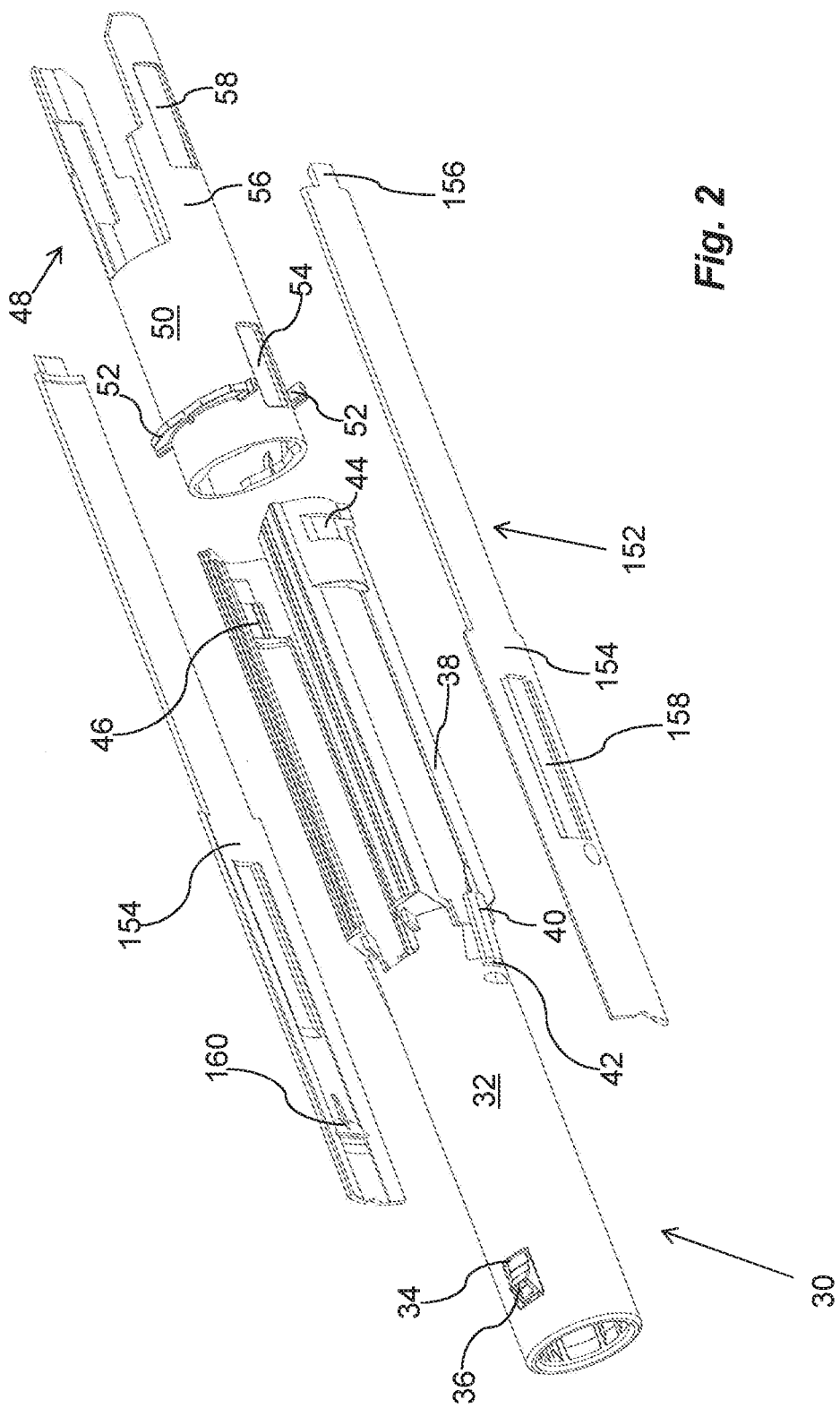
FIG. 2 is a detailed views of components comprised in the medicament delivery.

A medicament delivery member guard, in the embodiment shown comprising a front medicament delivery member guard 30 and a rear medicament delivery member guard 48 that are comprised in an activation mechanism as will be described, FIGS. 1 and 2, is further arranged slidable in the housing 10. The front medicament delivery member guard 30 is arranged with a proximal generally tubular part 32 that may protrude through the opening 26 at the proximal end of the housing. The tubular part 32 is arranged with proximally directed tongues 34 formed in the tubular part 32 by U-shaped cut-outs. The tongues 34 are flexible in the generally radial direction and are arranged with outwardly extending protrusions 36. At the distal end of the proximal part 32, two generally flat arms 38 are extending in the distal direction. At the junction between the proximal part 32 and the arms 38, tongues 40 are attached, which extend in the distal direction at some outwards inclination in relation to a longitudinal axis. The tongues 40 are designed and attached to the proximal part 32 such that proximal end surfaces 42 of the tongues 40 are created. At a distal end of the arms 38, cut-outs 44 are arranged. Further, protrusions 46 are positioned on the inner surface of the arms 38 proximal of and adjacent the cut-outs 44. Distally directed end surfaces of the protrusions 46 are arranged to abut proximal end surfaces of the rear medicament delivery member guard 48. The rear medicament delivery member guard 48 is arranged as a tubular body 50. At a proximal area of the tubular body 50, two radially extending ledges 52 are arranged around the circumference. Between the two ledges 52 are rectangular cut-outs 54 that extend in the longitudinal direction. At the distal end of the tubular body 50, two arms 56 are extending in the distal direction. The arms 56 are provided with rectangular cut-outs 58.

Figure 3:
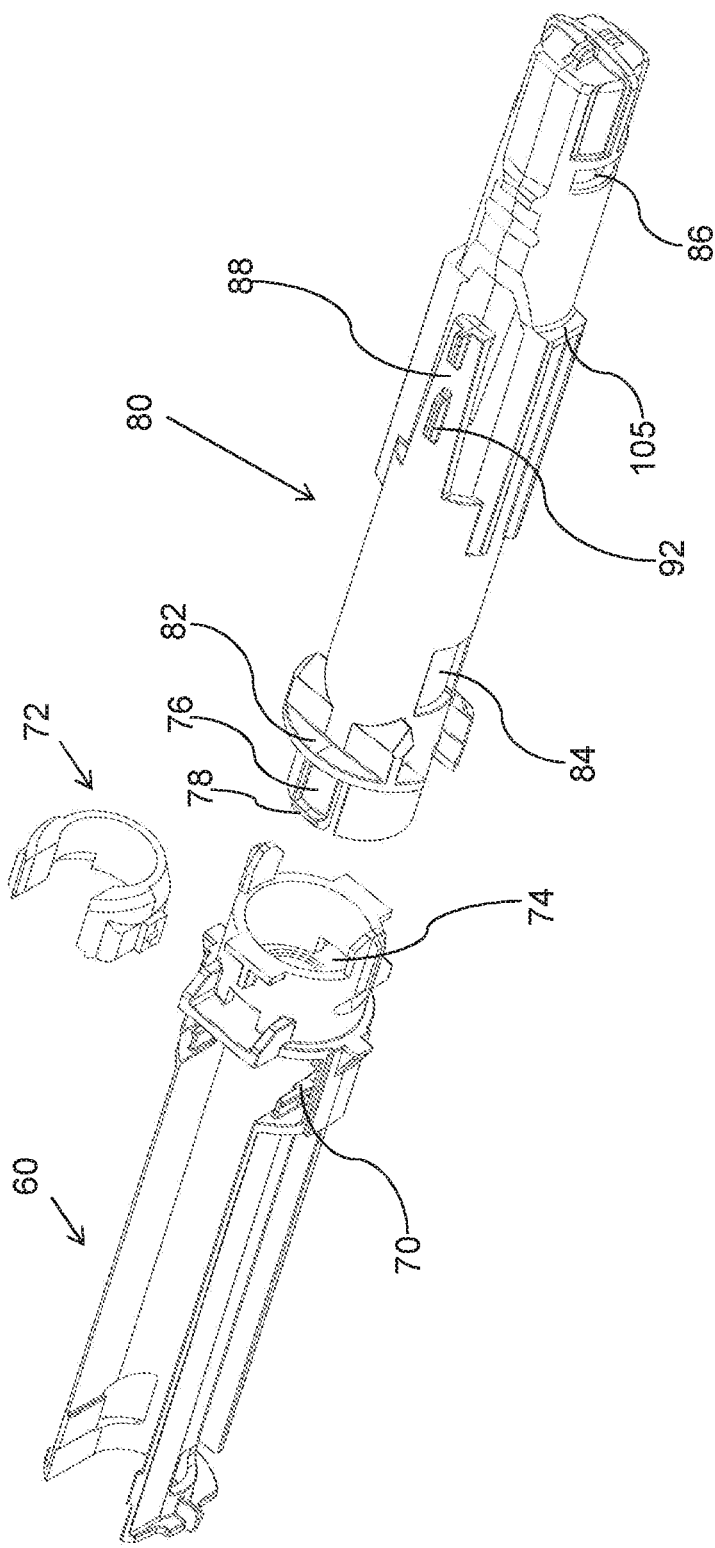
FIG. 3 is a detailed views of components comprised in the medicament delivery device of FIG. 1.

Further, inside and coaxial with the medicament delivery member guard 30 is a medicament container holder 60, FIGS. 1 and 3, having a general C-shape as seen in a cross-sectional view. The medicament container holder 60 is arranged to contain a medicament container 62 that in the embodiment shown is a generally elongated syringe with a fixed injection needle 64 at its proximal end and having a movable stopper 65 enclosing the distal end of the medicament container 62, FIG. 4. The injection needle 64 is preferably protected by a suitable medicament delivery member shield 66, FIG. 4a. In the embodiment shown the medicament delivery member shield 66 is a so called flexible needle shield or FNS. It is however to be understood that other types of medicament delivery member shields are feasible within the disclosure.

The distal end of the medicament container 62 is arranged with a generally radially extending flange 68, and the medicament container holder 60 is provided with a recess 70 in which the flange 68 fits, FIG. 3. In order to secure the medicament container 62 in the medicament container holder 60 a generally C-shaped clip 72 is arranged which is designed to fit into the recess 70 and to engage with the walls of the recess 70 in order to securely hold the medicament container 62 inside the medicament container holder 60. At the distal end of the medicament container holder 60, recesses 74 are arranged. These recesses 74 are designed to interact with proximally directed tongues 76 having outwardly directed ledges 78, which ledges 78 fit into the recesses 74. The proximally directed tongues 76 are attached to a generally tubular plunger holder 80, which plunger holder 80 is comprised in a power unit 81 of the medicament delivery device, shown in FIG. 5. Adjacent the attachment points of the tongues 76, generally radially extending ledges 82 are arranged. Further, cut-outs 84 are arranged on opposite sides of the body, having generally rectangular shapes. At the distal end of the plunger holder, two recesses 86 are arranged on opposite sides thereof.

Figure 6:
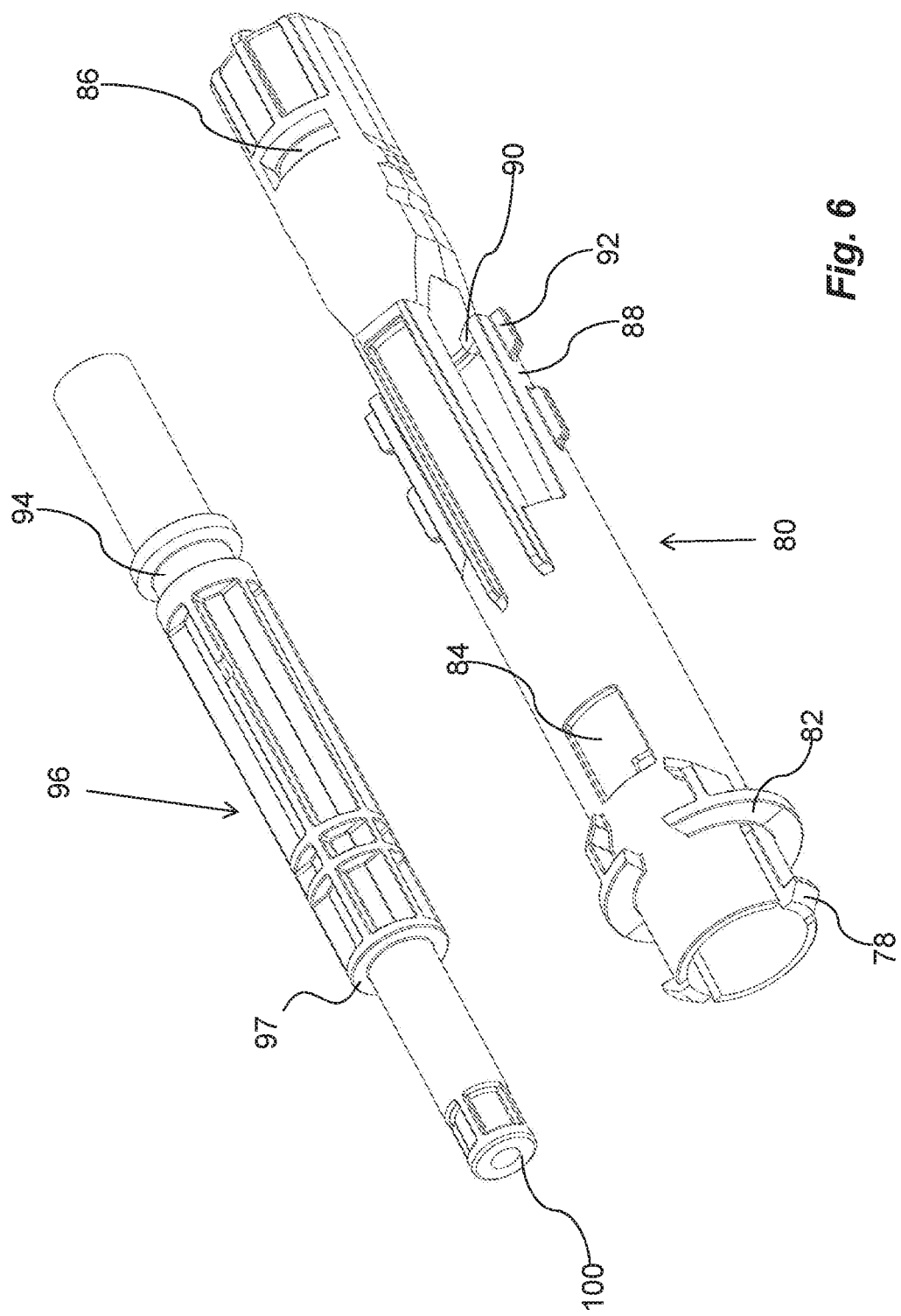
FIG. 6 is a detailed view of components comprised in the medicament delivery device of FIG. 1.

The plunger holder 80 is further arranged with two distally directed arms 88 on opposite sides that are flexible in the generally radial direction. The free ends of the arms 88 are arranged with inwardly directed ledges 90, FIG. 5, and outwardly directed surfaces of the arms 88 are arranged with radially directed protrusions 92. The inwardly directed ledges 90 are designed to interact with circumferential recesses 94 on an outer surface of an elongated plunger rod 96, FIG. 6, which plunger rod 96 is arranged slidable in a longitudinal direction inside the plunger holder 80. The plunger rod 96 is further arranged with a circumferential, proximally directed, ledge 97 positioned at a predetermined distance from the proximal end of the plunger rod. A drive spring 98, FIGS. 1 and 5, that in the embodiments shown is a compression spring is comprised in the power unit. The drive spring 98 is arranged between a proximal end wall 100 of the plunger rod 96 and a distal end wall 102 of the plunger holder 80, FIG. 5a. An elongated spring guide rod 104, FIG. 4a, is arranged inside the drive spring 98 for preventing buckling of the drive spring 98. Adjacent the free ends of the arms 88 two distally directed support ledges 105, FIG. 3, are arranged on opposite sides, the function of which will be described below.

Coaxial with, and positioned radially outside the plunger holder, is an actuator 106, FIGS. 7 to 9, having a generally tubular first body 108. At a distal end of the first body two distally directed arms 110 are arranged, being flexible in the generally radial direction. The free ends of the arms 110 are arranged with inwardly directed ledges 112. The ledges 112 of the arms are arranged to fit into the recesses 86 of the plunger holder 80 for releasably holding the plunger holder 80 as will be described below. Outside the tubular first body 108 and coaxial therewith is a tubular second body 114, where the bodies are attached to each other by longitudinally extending ribs 116. The second body 114 is arranged with two proximally directed tongues 118 that are flexible in the generally radial direction. The free ends of the tongues 118 are arranged with inwardly directed ledges 120. The second body 114 is arranged with longitudinally extending slits 122 which terminate at the proximal end surface of the second body 114. Further, end sections 124 are arranged between the first and the second bodies, which end sections 124 are arranged with two generally rectangular first passages 126 and a centrally positioned generally rectangular second passage 128.

The actuator is held stationary by an actuator lock 130 in the form of a generally U-shaped element. Proximally directed arms 132 of the actuator lock 130 are arranged with generally rectangular cut-outs 134 extending along the arms 132. Each cut-out 134 is provided with distally directed tongues 136 that have a certain outwardly inclination. The proximally directed arms 132 are designed to fit in the rectangular second passage 128 and the annular space between the first 108 and the second 114 bodies and extend such that the distal ends of the tongues 136 are designed to move out into the slits 122 of the second body and be resting with their end surfaces against proximally directed end surfaces of the slits 122, thereby locking them relative each other as seen in FIG. 7b.

An end cap 138 is further provided for the medicament delivery device, FIG. 8. It comprises a generally dome-shaped body 140 arranged to cover the distal end of the housing. A number of support beams 142 extend in the proximal direction, which support beams 142 are to rest against the distally directed surface of the end sections 124 of the actuator 106. Further two attachment arms 144 are extending from the body 140 in the proximal direction. The attachment arms 144 have a generally rectangular cross-sectional shape and are intended to fit into the generally rectangular first passages 126 of the end sections 124 of the actuator 106. At the proximal area of the attachment arms are generally rectangular cut-outs 146, which are intended to engage with the inwardly directed ledges 120 of the tongues 118 of the second body 114 of the actuator 106 such that they are locked to each other when the attachment arms 144 are pushed into the first passages 126. With this solution the actuator 106, the actuator lock 130 and the end cap 138 are thus locked to each other when assembled. The assembly is in turn attached to the distal end of the housing in that the inwardly directed ledges of the tongues 29 of the housing 10 fit into passages created around the arms of the second body as seen in FIG. 10.

A number of spring force elements are arranged in the power unit 81 shown in FIG. 5. A medicament delivery member guard spring 148 in the form of a compression spring is arranged between distally directed surfaces of the ledges 52 of the rear needle cover and proximally directed end surfaces of the longitudinal ribs 116 between the first and the second tubular bodies of the actuator 106. A penetration spring 150 also in the form of a compression spring is arranged between the distally directed support ledges 105 of the plunger holder 80 and proximally directed surfaces of the end sections 124 of the actuator 106.

Figure 12:
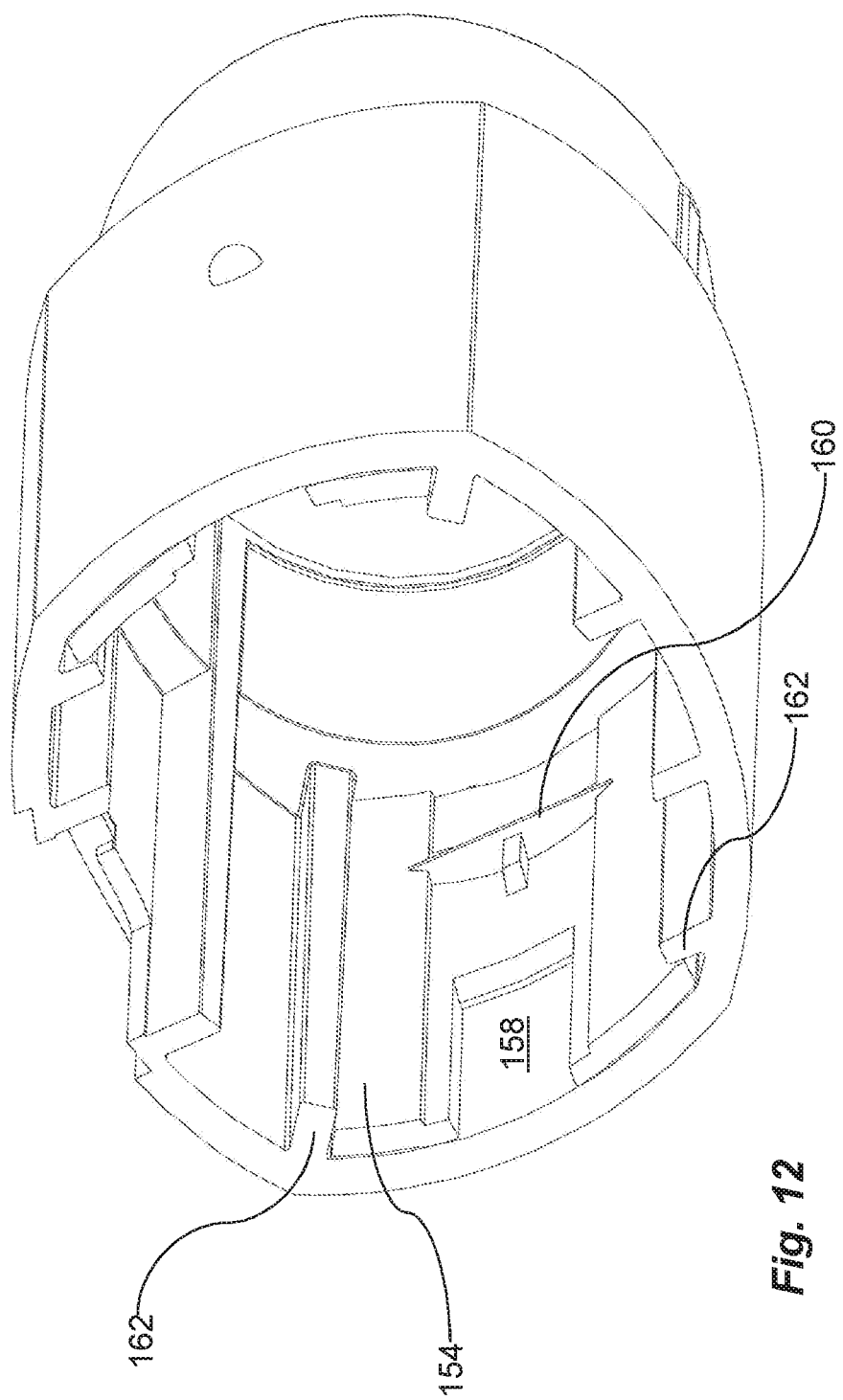
FIG. 12 is a detailed view of components comprised in the medicament delivery device of FIG. 1.

Further needle cover lock elements 152, FIGS. 2 and 11, are provided inside the housing of the medicament delivery device. The needle cover lock elements 152 comprise generally elongate plate-shaped members 154 that extend from a proximal end of the second body 114 of the actuator 106 to outside the needle cover as seen in FIG. 11a. The distal end of the members 154 are provided with cut-outs on each side such that a central part 156 fits into the slit 122 of the second body 114 where distally directed end surfaces of the cut-outs are resting on the proximal end surface of the second body 114 on each side of the slit 122, FIG. 11a. At the proximal area of the members 154 generally rectangular cut-outs 158 are provided, the function of which will be explained. On the inner surface of the members 154 at a proximal area thereof, FIGS. 2 and 12, transversal ledges 160 are arranged, designed to interact with the tongues 40 of the medicament delivery member guard 30 as will be described. The needle cover lock element 152 is supported in the proximal area by longitudinally extending guide ledges 162 on the inner surface of the housing 10. As seen in FIG. 12, the guide ledges 162 are arranged such that the needle cover lock element 152 is guided in all directions but the longitudinal.

Figure 13:
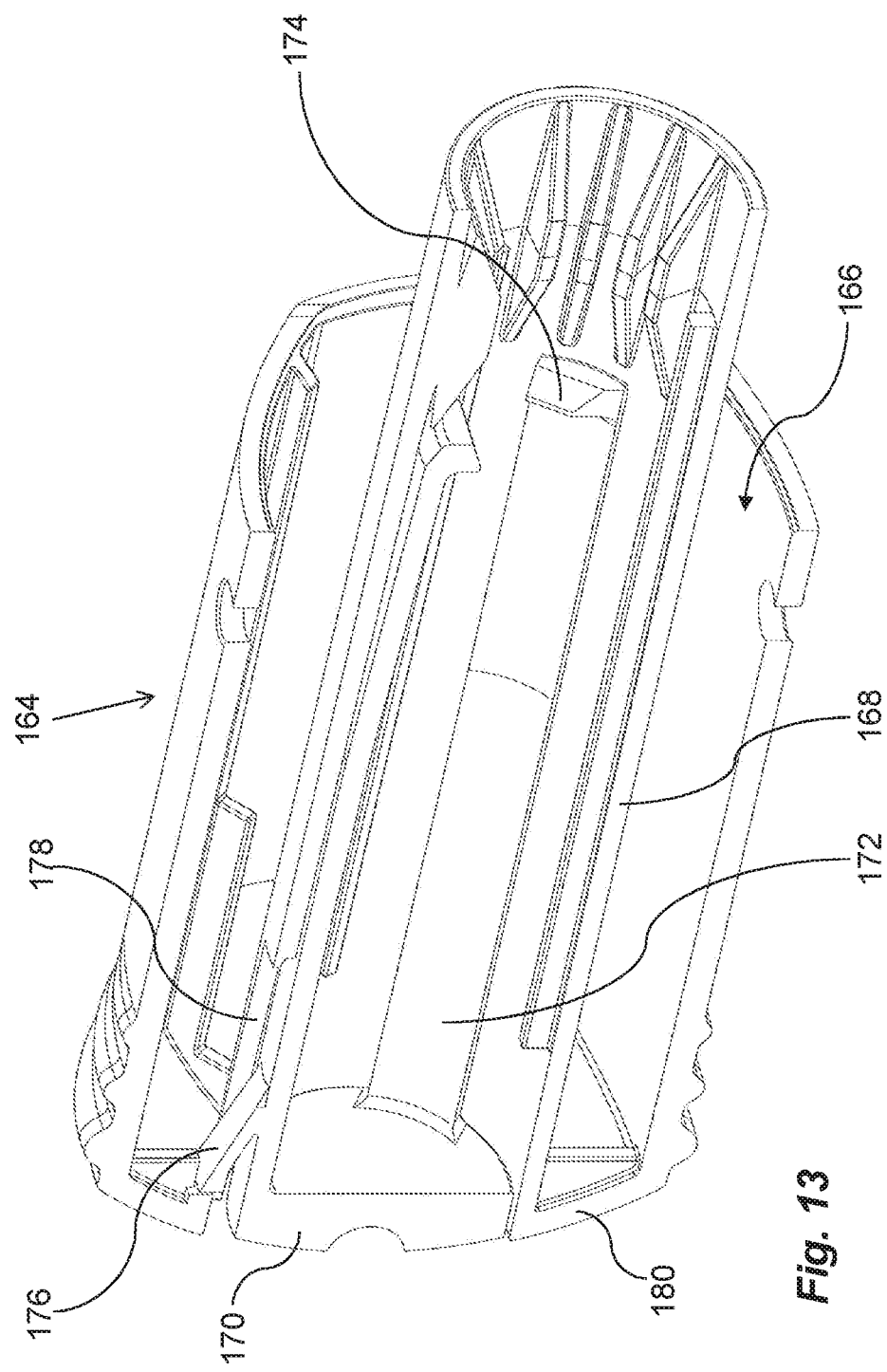
FIG. 13 is a detailed view of components comprised in the medicament delivery device of FIG. 1.

Further, the medicament delivery device is arranged with a front cap 164, FIGS. 1 and 13, arranged with a distally directed passage 166. The shape of the passage 166 is to fit onto the proximal section 16 of the housing with a friction fit to releasably hold the front cap 164 onto the housing 10. The front cap 164 is further arranged with a distally directed generally tubular body 168 having dimensions so as to fit into the proximal end of the medicament delivery member guard 30. Inside the tubular body a medicament delivery member shield remover is arranged. It comprises a plate-shaped body 170 arranged with three distally directed arms 172. The ends of the arms 172 are arranged with inwardly directed ledges 174, which ledges 174 are arranged to engage the outer surface of a medicament delivery member shield 66. The outer surfaces of the arms 172 are arranged with proximally directed, outwardly inclined, tongues 176, which tongues 176 are designed to fit into longitudinal slits 178 in the tubular body 168 such that the end surfaces of the tongues rest against a distally directed surface of an end wall 180 of the front cap 164.

The medicament delivery device is intended to function as follows. When the medicament delivery device is assembled, a medicament container 62, with a medicament delivery member shield 66 attached to the injection needle 64, is preferably inserted into the medicament container holder 60 and a C-clip 72 is attached so that the medicament container 62 is securely attached to the medicament container holder 60. A drive spring 98 is inserted into the plunger holder 80 and is tensioned by the plunger rod 96 being pushed in the distal direction into the plunger holder 80 until the ledges 90 of the arms 88 fit into the recesses 94 of the plunger rod 96. The first body 108 of the actuator 106 is then pushed onto the plunger holder 80 in the proximal direction until the ledges 112 of the arms 110 of the first body 108 fit into the recesses 86 of the plunger holder 80, whereby the arms 110 are prevented from flexing in the radial direction. The rear medicament delivery member guard 48 is then pushed onto the first body 108 of the actuator 106 such that the arms 88 of the first body 108 are prevented from flexing in the radial direction. Thus, a power pack 81 is formed.

The needle cover locks 152 are pushed from the distal end into the housing 10 of the medicament delivery device. In this regard, they are guided and supported in all transversal directions by the guide ledges 162 as seen in FIG. 12. The medicament delivery member guard 30 is then entered into the housing from the distal end, whereby the tongues 40 will slide on the inner surface of the needle cover lock elements 152 until they enter the cut-outs 158, where they will flex outwardly in the radial direction and be positioned in a non-tensioned state or condition in a delivery mode, FIG. 11*b*. The medicament container holder 60 is now attached to the plunger holder 80 and the whole assembly is inserted into the housing from the distal end, which causes the needle cover lock elements 152 to be locked in the longitudinal direction by the central part 156 at the distal end of the needle cover locks fitting into the slits 122 of the actuator, FIG. 11*a*. Then the distal end of the medicament delivery device is closed by the actuator lock 130 and the end cap 138. Further, a front cap 164 is attached to the proximal end of the medicament delivery device.

Figure 14:
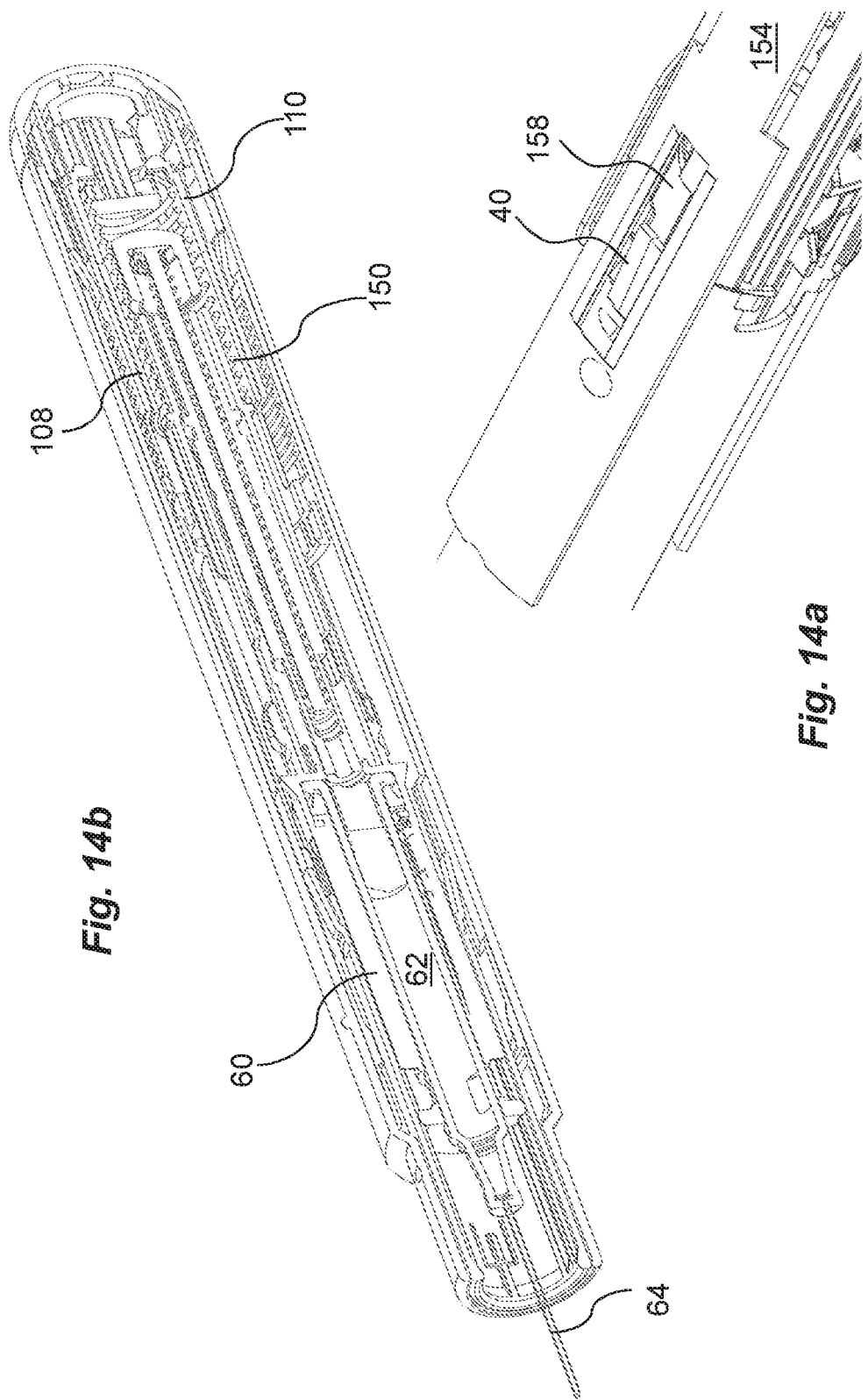
FIG. 14 is a view of a different functional stage of the medicament delivery device of FIG. 1.

When the medicament delivery device is to be used, the front cap 164 is removed by pulling it in the proximal direction. The ledges 174 of the medicament delivery member shield grabber engage the material of the medicament delivery member shield 66 so that the medicament delivery member shield 66 is also pulled off when the front cap 164 is removed. The device is now ready to deliver a dose of medicament. The proximal end of the medicament delivery device is then pressed against a dose delivery site, i.e. the proximal end of the front medicament delivery member guard. This causes the front medicament delivery member guard 30 to move distally in relation to the housing and because the front medicament delivery member guard 30 is connected to the rear medicament delivery member guard 48, the latter will also move in the distal direction in relation to the housing. Further, the tongues 40 move non-tensioned in the recesses 158 of the members 154 of the needle cover locks 152, FIG. 14*a*. When the medicament delivery member guard has moved a certain distance, the rectangular cut-outs 58 of the rear medicament delivery member guard 48 will be positioned radially outside the arms 110 of the first body 108 of the actuator 106, which arms 110 are then free to flex radially outwards, thereby releasing the plunger holder 80. The plunger holder 80 is now moved in the proximal direction by the force of the penetration spring 150, whereby the medicament container holder 60 with its medicament container 62 is also moved in the proximal direction, causing a penetration by the injection needle 64 into the dose delivery site, FIG. 14*b*.

Figure 15:
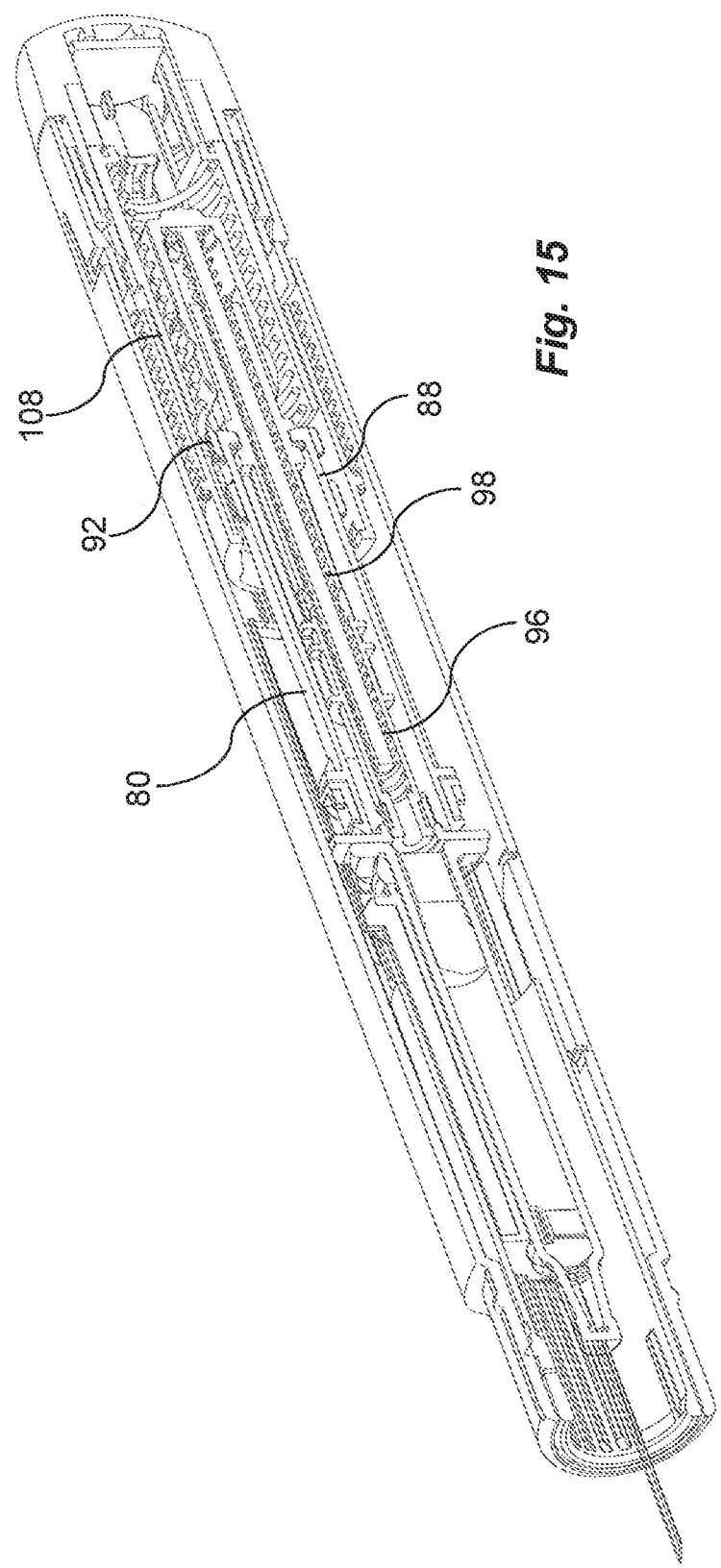
FIG. 15 is a view of a different functional stage of the medicament delivery device of FIG. 1

As the plunger holder 80 is moving in the proximal direction during the penetration sequence, it will also move in relation to the first body 108 of the actuator 106. At the end of the penetration movement, the protrusions 92 of the arms 88 of the plunger holder 80 holding the plunger rod 96 will pass out of contact with the inner surface of the first body 108, FIG. 15, wherein the arms 88 are free to flex radially outwards, releasing the plunger rod 96. Because of the drive spring 98, the plunger rod 96 is now urged in the proximal direction, whereby the stopper 65 of the medicament container 62 is also moved in the proximal direction, causing a dose of medicament to be delivered through the injection needle 64. The dose delivery sequence is terminated when the proximal circumferential ledge 97 of the plunger rod 96 comes in contact with a distal end surface of the medicament container holder 60, FIG. 16.

The medicament delivery device can now be removed from the dose delivery site. This enables the medicament delivery member guard 30, to be moved in the proximal direction relative the housing by the medicament delivery member guard spring 148 such that the injection needle 64 is covered by the medicament delivery member guard 30, FIG. 17. The movement of the medicament delivery member guard 30 is stopped when the proximally directed end surfaces 42 of the inclined tongues 40 of the medicament delivery member guard 30 come in contact with the transitional wall 20 of the housing, FIG. 18. The movement of the medicament delivery member guard 30 will also cause the inclined tongues 40 of the medicament delivery member guard 30 to move past the ledges 160 of the needle cover lock elements 152, which will prevent any movement of the medicament delivery member guard 30 in the distal direction in relation to the housing, thereby preventing any exposure of the injection needle 64. The medicament delivery device can now be discarded.

It is to be understood that the disclosure described above and shown in the drawings is to be regarded only as a non-limiting example and that it may be modified in many ways within the scope of the patent claims.

The invention claimed is:

1. A medicament delivery device comprising
a housing;
a medicament container holder arranged to accommodate a medicament container provided with a medicament delivery member;
a power unit arranged to act on said medicament container for expelling a dose of medicament when activated;
an activation mechanism operably connected to said power unit, capable of activating said power unit;
said activation mechanism comprising a medicament delivery member guard movable in a longitudinal direction in relation to said housing;
said activation mechanism comprising a force element arranged to bias said medicament delivery member guard to a proximal extended position wherein said medicament delivery member is covered; and
a locking mechanism operably arranged to lock said medicament delivery member guard in the extended position;
wherein said locking mechanism comprises a number of locking elements connected to said medicament delivery member guard and flexible in a generally radial direction,
wherein said locking mechanism further comprises a number of ledge surfaces connected to and axially fixed relative to said housing, wherein said locking elements flex radially outwards and abut said ledge surfaces when said medicament delivery member guard is moved in the extended position, preventing any further movement of said medicament delivery member guard in a distal direction, and
wherein recesses or cutouts are positioned and axially fixed relative to said housing, wherein said locking elements are positioned in a non-tensioned state prior to a delivery of a dose of medicament.

2. The medicament delivery device according to claim 1, wherein said recesses or cutouts are arranged on a separate component attached inside the housing of said medicament delivery device.

3. The medicament delivery device according to claim 2, wherein said separate component is releasbly attached to said housing of said medicament delivery device.

4. The medicament delivery device according to claim 2, wherein said separate component comprises an elongated plate-shaped member.

5. The medicament delivery device according to claim 4, wherein said housing is arranged with support elements preventing movement of said separate component when assembled.

6. The medicament delivery device according to claim 5, wherein the support elements comprises a transversal stop element arranged to abut a proximal end of the separate component.

7. The medicament delivery device according to claim 6, wherein the transversal stop element is comprised in the housing.

8. The medicament delivery device according to claim 5, wherein the support elements comprise longitudinally extending ledges arranged to support the separate component in all transversal directions.

9. The medicament delivery device according to claim 5, wherein the support elements comprise a transversal stop element arranged to abut a distal end of the separate component.

10. The medicament delivery device according to claim 7, wherein the support element is comprised in a component attachable to the housing.

11. The medicament delivery device according to claim 2, wherein the separate component comprises the said ledge surfaces.

12. A medicament delivery device comprising:
a housing;
an activation mechanism operably connected to a power unit, where the activation mechanism comprises a medicament delivery member guard movable in a longitudinal direction in relation to the housing; and
a locking mechanism that locks the medicament delivery member guard in an extended position after dose delivery, the locking mechanism comprises a locking element positioned on the medicament delivery member guard and being flexible in a radial direction, where the locking mechanism further comprises a ledge surface axially fixed relative to the housing,
wherein the locking element flexes radially outward and abuts the ledge surface when the medicament delivery member guard is moved to the extended position such that further movement of the medicament delivery member guard in the distal direction is prevented,
wherein recesses or cutouts are positioned and axially fixed relative to the housing, and
wherein the locking element is positioned in a non-tensioned state prior to a delivery of a dose of medicament.

13. The medicament delivery device according to claim 12, wherein the recesses or cutouts are arranged on a separate component fixedly attached to an inside surface of the housing and is prevented from axial movement by a support element.

14. The medicament delivery device according to claim 13, wherein the support element comprises a transversal stop element arranged to abut a distal end of the separate component.

15. The medicament delivery device according to claim 14, wherein the ledge surface is located on the separate component.

16. The medicament delivery device according to claim 1, wherein said locking elements are positioned in the non-tensioned state during delivery of the dose of medicament such that said locking elements move non-tensioned in the recesses or cutouts during delivery of the dose of medicament.

17. The medicament delivery device according to claim 14, wherein the locking element is positioned in the non-tensioned state during during delivery of the dose of medicament such that the locking element moves non-tensioned in the recesses or cutouts during delivery of the dose of medicament.

* * * * *